United States Patent [19]
Horn

[11] Patent Number: 5,718,245
[45] Date of Patent: Feb. 17, 1998

[54] FIRST AID TREATMENT INCORPORATING UNIVERSAL PRECAUTIONS AND CONTAINMENT OF INFECTIOUS BODY FLUIDS

[76] Inventor: Rodney K. Horn, 1504 Eleventh St., Wichita Falls, Tex. 76301

[21] Appl. No.: 358,408

[22] Filed: Dec. 19, 1994

[51] Int. Cl.⁶ .................................................. A61B 19/00
[52] U.S. Cl. ............................................ 128/897; 206/570
[58] Field of Search ...................... 128/897–98; 206/570, 206/803

[56] References Cited

U.S. PATENT DOCUMENTS

| | | | |
|---|---|---|---|
| 4,657,804 | 4/1987 | Mays et al. | 428/212 |
| 4,917,238 | 4/1990 | Schumacher | 206/570 |
| 5,117,981 | 6/1992 | Crawford et al. | 206/570 |
| 5,392,917 | 2/1995 | Alpern et al. | 206/570 |

*Primary Examiner*—John P. Lacyk
*Attorney, Agent, or Firm*—Jerry C. Ray

[57] ABSTRACT

A self-contained, single-use precautionary infection control kit of supplies and material for first aid treatment of open injuries has protective gloves, supplies for treating and covering a wound, and a closeable bag for containing and disposing of all material used in the treatment. The kit is packaged in a sterile, flexible, crushable package which is sized to be carried in a pocket, and which has a peelable cover with printed instructions.

2 Claims, 3 Drawing Sheets

5,718,245

FIRST AID TREATMENT INCORPORATING UNIVERSAL PRECAUTIONS AND CONTAINMENT OF INFECTIOUS BODY FLUIDS

CROSS REFERENCE TO RELATED APPLICATIONS

None.

BACKGROUND OF THE INVENTION

1. Field of the Invention

This invention relates to containment of infectious bodily fluids, and more particularly to containment and disposal of first-aid materials contaminated by blood and other bodily fluids in first-aid situations.

2. Description of the Related Art

The dangers of infection from AIDS and other diseases which are transmitted by contact with bodily fluids are well known. It is a common practice for medical personnel and others treating open wounds in the human body to wear gloves and other protective gear. Protective measures are necessary because a person requiring treatment may unknowingly be a carrier of the Human Immunodeficiency Virus (HIV). In some instances the victim of an accident may be unconscious and unable to warn others of possible hazards of infection.

A specific danger lies in the treatment of wounds in a first-aid situation; football, soccer, and other sports trainers and medical technicians often treat wounds on a practice field or playing field. Typically, the first aid is rendered using medical supplies from a field kit or bag containing a variety of such first-aid supplies. The person administering first aid will reach into the bag several times during the course of the treatment to remove dressings, medications, etc. The danger is that materials in the bag may become contaminated with blood from the victim, and thus become the vehicle by which infectious diseases are spread to others who are treated later from the same kit.

A need exists, therefore, for a self-contained, single-use kit for first aid treatment of open wounds which minimizes or eliminates the risk of contact with body fluids. Such a kit protects not only the care-giver and the victim, but also provides for containment of materials contaminated with body fluids so that others are not placed at risk of being contacted by them. This approach is embodied in the concept of universal precautions, where all body fluids and other tissue are treated as possible sources of infection. In the past, protective gear was worn to protect the victim from infection; today, universal precautions require protection not only of the victim, but also the person giving treatment and others who might come in contact with treatment materials.

Of the patents listed below, Kalb discloses a method of treating and disposing of blood-contaminated materials such as menstrual pads or tampons. Crawford et al. disclose a method of rolling gloves compactly so they will fit into a small container. Schumacher discloses a waste cleanup kit having absorbent and disinfectant materials. None of these, however, disclose a single-use medical kit having the contents arranged in order of use, together with means for disposing of contaminated materials.

Applicant is aware of the following U.S. patents which were disclosed by a pre-examination search:

| Patent No. | Issue Date | Patentee |
|---|---|---|
| 2,952,354 | Sep. 13, 1960 | Whitelaw et al. |
| 3,698,549 | Oct. 17, 1972 | Glassman |
| 3,770,119 | Nov. 6, 1973 | Hultberg, et al. |
| 4,702,378 | Oct. 27, 1987 | Finkel et al. |
| 4,917,238 | Apr. 17, 1990 | Schumacher |
| 5,117,981 | Jun. 2, 1992 | Crawford et al. |
| 5,287,960 | Feb. 22, 1994 | Kalb et al. |

SUMMARY OF THE INVENTION

The invention is a precautionary infection control kit, designated herein by the acronym PICK, which is a single-use kit for the first-aid treatment of open injuries. Supplies and materials for treatment are packaged in the kit in the order in which they are used.

By using such a kit, the problem of contamination of supplies in a larger kit is eliminated. All materials used in the treatment of a single patient, including protective gloves worn by the person administering first aid, are placed in a closeable, impermeable bag after they are used. When the treatment is finished, the last item to go into the containment bag will be antiseptic towelettes used to clean the care-giver's hands. The bag is then closed and labeled with a bio-hazard label for subsequent disposal in an appropriate manner.

For treatment of subsequent injuries, another PICK is used, so that all materials used for each treatment are sterile and are contained for disposal as soon as each treatment is completed. This method of treating injuries using a self-contained, single-use kit incorporates universal precautions standards by treating all body fluids and tissue as potentially infectious.

It is a primary object of this invention to provide a method for treating wounds which includes a method of containing materials contaminated with bodily fluids.

Another object is to provide a single-use precautionary infection control kit (called a PICK) containing sterile materials for treating wounds and also containing means for containment and disposal of materials contaminated with body fluids, to maintain universal precautions against spreading infection.

A further object is to provide such a kit in a flexible, crushable, sterile package which can be carried in a clothing pocket.

Further objects are to achieve the above with a method that is rapid, versatile, efficient, and inexpensive, and with devices that are compact, durable, lightweight, simple, safe, efficient, versatile, and reliable.

The specific nature of the invention, as well as other objects, uses, and advantages thereof, will clearly appear from the following description and from the accompanying drawings, the different views of which are not necessarily scale drawings.

CATALOG OF THE ELEMENTS

Figure 1:
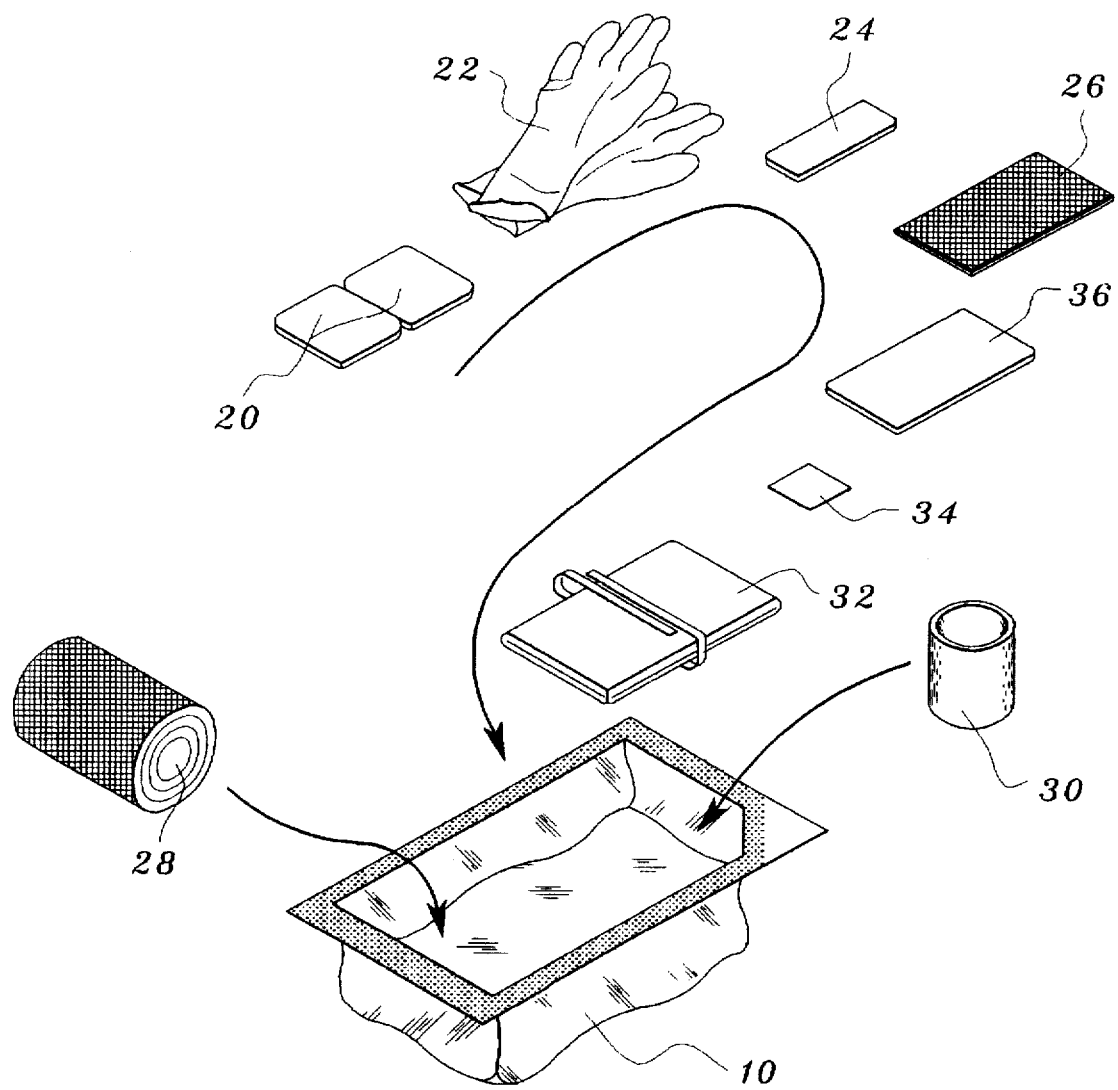
FIG. 1 is an exploded view of the contents of the kit with the cover removed.

As an aid to correlating the elements of the invention with the exemplary drawings, the following catalog of the elements is provided:

10 package
12 package cover
20 gauze sponges
22 gloves
24 disinfectant swabstick
26 non-adherent pad
28 stretch gauze
30 tape
32 closeable bag
34 biohazard label
36 anti-microbial wipes

DESCRIPTION OF THE PREFERRED EMBODIMENTS

Figure 2:
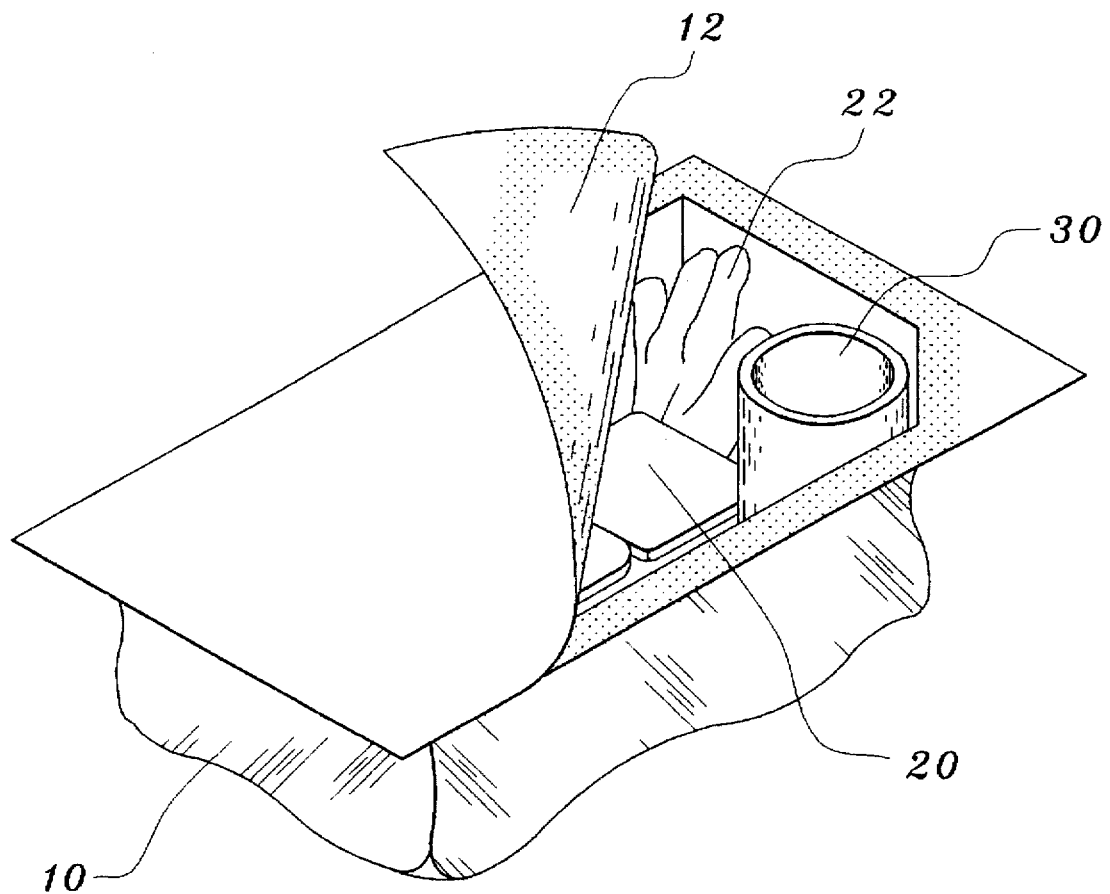
FIG. 2 shows the kit with the cover partially peeled away, and some of the contents.
Figure 3:
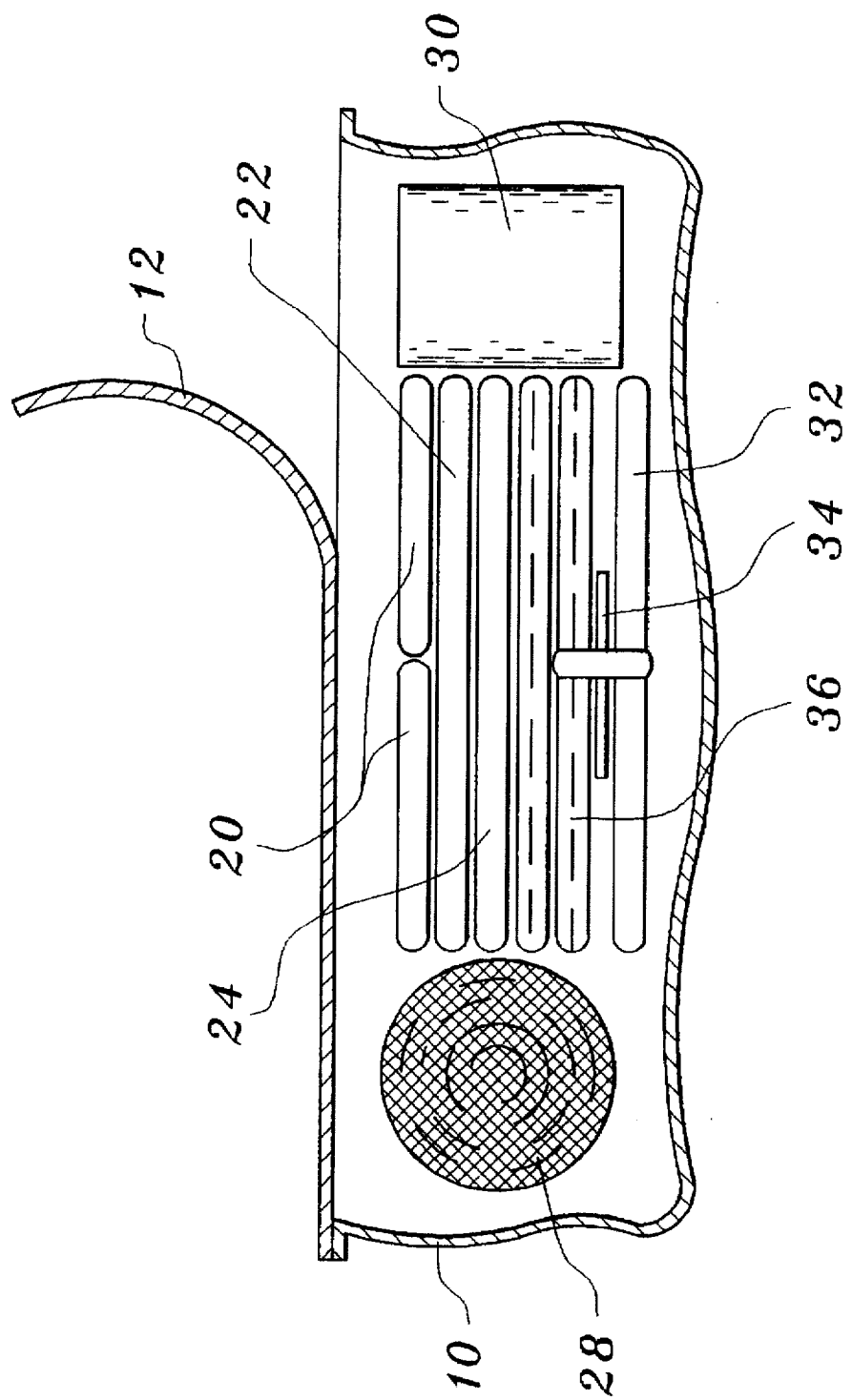
FIG. 3 is a side elevation of the kit with the cover partially peeled back; the contents are shown schematically.

The invention comprises materials for treating an open wound packed in specific order within a compact package, and the method for their use. Referring to FIGS. 1, 2, and 3, the package is pocket-sized, sterilizable, crushable, and flexible. The precautionary infection control kit is housed in a package 10 made from resilient plastic film, with a peelable cover 12. The plastic film defines a flexible basin which contains the first-aid supplies and materials. The package is designed to fit into a pocket in a person's clothing; in one embodiment the approximate dimensions of the package are: length 6.25 in., width 3.5 in., and depth 1.75 in.

Made from a material which is permeable to air, cover 12 allows air to escape from the package 10. Escape of air becomes important when the package is subject to compression, as it would be if carried in a clothing pocket. Because air can escape from the package through the cover, air pressure inside the package due to compression is reduced. The result is that both the package and the cover resist rupturing which would destroy the integrity of the package.

After the various supplies and materials described below are placed in the package, the interior of the package and its contents are sterilized by methods known to those skilled in packaging medical supplies. Sterility of the supplies inside the package is maintained by using a material for the peelable cover which, though permeable to air, will block the passage of micro-organisms such as bacteria.

Medical first aid supplies are placed within the package 10 in the order of their use, so that when the package is opened by removing the peelable cover, the item on top is one or more gauze sponges 20. The gauze sponges are used as required for applying pressure to the wound to stop bleeding. In many situations, the sponges will be handed to the victim who will apply pressure to the wound while the person administering treatment dons protective gloves 22, which are located in the package immediately below gauze sponges 20. In instances where the victim cannot apply pressure to the wound, the person administering treatment may easily remove gloves 22 from beneath the sponges and put on the gloves before beginning the treatment.

Beneath the protective gloves is a disinfectant swabstick 24 which is used to clean the wound area. In one embodiment, the disinfectant swabstick is a PVP swabstick in which polyvinyl pyrrolidone is a carrier for the disinfecting agent. Other suitable disinfectants are useful as well.

The next item in the PICK are one or more non-adherent pads 26 for covering the wound after bleeding has been suppressed. The non-adherent pads 26 are held in place over the wound by wrapping with a piece of stretch gauze 28; the gauze is in turn is secured by adhesive tape 30, which is packed at one end of the PICK package 10.

With the wound cleaned and covered, all materials used in the treatment are placed in a bag 32 which is packed second-from-bottom in the package as shown in FIG. 1 and FIG. 3. Then the person administering treatment removes the protective gloves 22 and places the gloves in the bag 32.

Remaining in the PICK are two or more anti-microbial wipes 36; one is used to clean the hands of the person giving treatment, and one is used by the victim to clean hands or other contaminated parts of the victim's body. Anti-microbial wipes, as used herein, includes antibacterial towelettes and other applicable types of antiseptic wipes.

After the wipes or towelettes are placed into the disposal bag, the bag is closed with a tie or by other means. A bio-hazard label 34 is placed on the bag 32 to mark it as a source of possible infection. The labeled bag and its contents are then disposed of in a safe manner; the method of disposal may vary depending on the place and circumstances of use of the PICK.

The method of preventing the spread of infectious diseases during treatment of open injuries has been partially described above together with the apparatus comprising the invention. Steps in the method include treating an injured person with a self-contained, single-use kit for infection control as described above, where the kit contains means for containing the materials which become contaminated with body fluids such as blood during the treatment.

Containing the materials which become contaminated with body fluids is the next step; the preferred method of containment is use of a closeable, impermeable bag 32, marked with a bio-hazard label 34, in which the contaminated material and supplies are placed for subsequent disposal. In one embodiment the bag is closed with a twistable tie; alternatively the bag may have a plastic closer with opposing tracks which engage each other to form a seal. The importance of this step is that it prevents contaminated material from coming in contact with, and contaminating, other first-aid supplies, or the surrounding environment.

The method is repeated for other injuries, so that each injured person is treated with sterile materials from an individual single-use precautionary infection control kit. At no time during the above-described procedure is there any transfer of first-aid supplies to or from a larger supply kit, and therefore no risk of contaminating supplies in such a kit.

The embodiments shown and described above are only exemplary. I do not claim to have invented all the parts, elements, or steps described. Various modifications can be made in the construction, material, arrangement, and operation, and still be within the scope of my invention.

The restrictive description and drawing of the specific examples above do not point out what an infringement of this patent would be, but are to enable one skilled in the art to make and use the invention. The limits of the invention and the bounds of the patent protection are measured by and defined in the following claims.

I claim as my invention:

1. A kit for treating injuries and for containing infectious body fluids resulting from said injuries, comprising:
    a) a single-use first aid kit packaged in a sterile, flexible, crushable package,
    b) said kit including medical first aid supplies packed in said kit in order of use, said first aid supplies including
    c) one or more protective gloves,
    d) at least one roll of medical tape, e) at least one piece of stretch gauze,
f) two or more anti-microbial wipes,
g) at least one antiseptic swabstick,
h) one or more gauze sponges,
i) one or more non-adherent pads,
j) a waste bag made from impermeable plastic for containing for subsequent disposal, material contaminated with body fluids,
k) at least one bio-hazard label for placing on said waste bag,
l) a tie for closing said waste bag;
m) said package including a container portion and a cover portion,
n) said container portion made from a resilient plastic,
o) said cover portion made from a material which is permeable to air and impermeable to microorganisms, and
p) said flexible, crushable package having dimensions allowing said package to be carried in a pocket in a person's clothing.

2. A method of preventing the spread of infectious diseases during treatment of open injuries and during disposal of treatment materials, comprising:

a) treating an injured person with a self-contained infection control kit, said kit containing supplies for a single treatment of an open injury and said kit including means for containing materials contaminated by body fluids during said treatment, said supplies placed in a package in order of removal and use, b) removing said treatment supplies from said package in a sequence determined by a placement of said supplies in said package, c) placing said treatment materials in a closeable, impermeable waste bag as said treatment materials are used, d) disposing of said materials contaminated with body fluids, and e) treating other injured persons with other individual single-use treatment kits.

* * * * *